(12) United States Patent
Hayasaka et al.

(10) Patent No.: US 11,859,166 B2
(45) Date of Patent: Jan. 2, 2024

(54) CALCULATION DEVICE, CONTROL DEVICE, CULTURE SYSTEM, AND METHOD FOR DESIGNING CULTURE SYSTEM

(71) Applicant: JGC JAPAN CORPORATION, Kanagawa (JP)

(72) Inventors: Wataru Hayasaka, Kanagawa (JP); Natsumi Yamada, Kanagawa (JP); Naoki Tahara, Kanagawa (JP)

(73) Assignee: JGC JAPAN CORPORATION, Kanagawa (JP)

( * ) Notice: Subject to any disclaimer, the term of this patent is extended or adjusted under 35 U.S.C. 154(b) by 0 days.

(21) Appl. No.: 18/026,125

(22) PCT Filed: Aug. 17, 2021

(86) PCT No.: PCT/JP2021/029994
§ 371 (c)(1),
(2) Date: Mar. 14, 2023

(87) PCT Pub. No.: WO2023/021571
PCT Pub. Date: Feb. 23, 2023

(65) Prior Publication Data
US 2023/0348837 A1  Nov. 2, 2023

(51) Int. Cl.
*C12M 1/34* (2006.01)
*C12M 1/00* (2006.01)

(52) U.S. Cl.
CPC ............ *C12M 41/34* (2013.01); *C12M 29/06* (2013.01)

(58) Field of Classification Search
CPC .............................. C12M 41/34; C12M 29/06

USPC ....................................................... 435/286.7
See application file for complete search history.

(56) References Cited

FOREIGN PATENT DOCUMENTS

| EP | 1705243 A1 | * 9/2006 | ............ C12M 41/48 |
|---|---|---|---|
| JP | H07203945 A | * 8/1995 | ............ C12M 29/06 |
| JP | 2006296423 | 11/2006 | |
| JP | 2008161850 | 7/2008 | |
| JP | 2019129726 | 8/2019 | |

OTHER PUBLICATIONS

Machine Translation of JP-H07203945-A (Year: 2023).*
(Continued)

*Primary Examiner* — Michael L Hobbs
(74) *Attorney, Agent, or Firm* — JCIPRNET (57) ABSTRACT

A calculation device (10) includes a calculation unit (14) that: acquires culture data over time indicating a relationship between a DO value detected in a culture solution and an oxygen supply amount controlled by a freely-selected control method, the culture solution being stored in a first culture tank (2) in which a culturing target material is cultured; identifies a culture model indicating a relationship between the oxygen supply amount for the culturing target material increasing over time and the DO value, based on the culture data; and executes simulation of virtually culturing the culturing target material in a second culture tank (20) using a culture control method of culturing the culturing target material based on the culture model and the oxygen supply amount in the second culture tank, and calculates parameters to be used in the culture control method based on the simulation result.

13 Claims, 4 Drawing Sheets

(56) References Cited

OTHER PUBLICATIONS

"International Search Report (Form PCT/ISA/210) of PCT/JP2021/029994", dated Oct. 5, 2021, with English translation thereof, pp. 1-6.

Naoki Tahara et al., "The development and implementation of a new bioreactor named "VerSus Reactor*" for mammalian cell culture," Pham Tech Japan, vol. 31, Oct. 2015, with English translation thereof, pp. 1-14.

Naoki Tahara, "Biopharmaceutical process/Bioengineering technologies for antibody drug production (1st Cell culture/Cell separation technologies)," Pham Tech Japan, vol. 28, Jul. 2012, with English translation thereof, pp. 1-12.

Igor Škrjanc, "Adaptive Supervisory Predictive Control of a Hybrid Fed-Batch Reactor with Slow Actuator," Industrial & Engineering Chemistry Research, vol. 46, Aug. 2007, pp. 8050-8057.

Christopher J. Hewitt et al., "The Scale-Up of Microbial Batch and Fed-Batch Fermentation Processes," Advances in Applied Microbiology, vol. 62, Feb. 2007, pp. 105-135.

Christos Chatzidoukas et al., "Development of a structured dynamic model for the production of polyhydroxybutyrate (PHB) in Azohydromonas lata cultures," Biochemical Engineering Journal, vol. 71, Feb. 2013, pp. 72-80.

\* cited by examiner

CALCULATION DEVICE, CONTROL DEVICE, CULTURE SYSTEM, AND METHOD FOR DESIGNING CULTURE SYSTEM

CROSS-REFERENCE TO RELATED APPLICATION

This application is a 371 application of the International PCT application serial no. PCT/JP2021/029994, filed on Aug. 17, 2021. The entirety of the above-mentioned patent application is hereby incorporated by reference herein and made a part of this specification.

TECHNICAL FIELD

The present invention relates to a calculation device, a control device, and a culture system for controlling a culture tank in which a culturing target material is cultured, and a method for designing the culture system.

BACKGROUND ART

When a culturing target material such as animal cells or microorganisms is cultured in a culture tank, the amount of dissolved oxygen (DO) in the culture tank is controlled. DO control is continuously performed for a long time, and has a property that the oxygen consumption amount increases as the culturing target material grows with the lapse of time (see, for example, Patent Literature 1). In the DO control in the culture tank, unlike the mechanical control, the amount of dissolved oxygen does not immediately follow the target value with respect to the control amount for supplying oxygen, and a dead time until the control target amount actually appears with respect to the target value occurs. In addition, the DO control has a property that a large response delay occurs until a DO value that is a control target amount appears with respect to an oxygen supply amount that is a given control amount.

CITATION LIST

Patent Literature

Patent Literature 1: JP 2008-161850 A

SUMMARY OF INVENTION

Technical Problem

In a case where an experiment is performed using an actual culture tank in order to calculate a control value of the amount of dissolved oxygen required for a culturing target material in the culture tank, there is a problem that the scale of the experiment is large, a large amount of cost is required, and a long period of time is required to acquire data.

An object of the present invention is to provide a calculation device, a control device, a culture system, and a method for designing the culture system capable of calculating a control value of an amount of dissolved oxygen in a culture tank without performing an actual culture experiment of a culturing target material in the culture tank.

Solution to Problem

The present invention provides a calculation device including a calculation unit configured to: acquire culture data over time indicating a relationship between a DO value detected in a culture solution and an oxygen supply amount controlled by a freely-selected control method, the culture solution being stored in a first culture tank in which a culturing target material is cultured; identify a culture model indicating a relationship between the oxygen supply amount for the culturing target material increasing over time and the DO value, based on the culture data; and execute simulation of virtually culturing the culturing target material in a second culture tank using a culture control method of culturing the culturing target material based on the culture model and the oxygen supply amount in the second culture tank, and calculate parameters to be used in the culture control method based on the simulation result.

According to the present invention, by identifying a culture model based on culture data obtained in a first culture tank and executing simulation for controlling a second culture tank based on the culture model, it is possible to adjust parameters of a control method in the second culture tank without actually performing a culture experiment of a culturing target material in the second culture tank, and it is possible to greatly reduce the cost required for the experiment.

In addition, the calculation unit may repeatedly execute the simulation and adjust the parameters based on a relationship between the oxygen supply amount virtually controlled based on the culture control method and the DO value detected in the second culture tank.

According to the present invention, it is possible to adjust parameters used in a control method in simulation without limiting the number of times without actually performing a culture experiment of a culturing target material in the second culture tank, to acquire appropriate parameters, and to significantly reduce the cost required for the experiment.

Further, the present invention provides control device in which a program for executing the culture control method in the calculation device is installed, the control device including: a control unit that controls the oxygen supply amount based on the culture control method to which the parameters are applied in the actual second culture tank after the parameters are input, and adjusts the DO value in the second culture tank to a preset setting value.

According to the present invention, in the control device that actually controls the second culture tank, since the parameters of the control method are adjusted in advance by the calculation device, the second culture tank can be accurately controlled together with the start of operation of the second culture tank without performing an actual culture experiment in the second culture tank.

In addition, the control unit may control a sparger that releases fine bubbles into the second culture tank to adjust the oxygen supply amount.

According to the present invention, the DO value in the second culture tank can be adjusted by the control device controlling the sparger.

The present invention also provides a culture system including: the calculation device; the control device; the second culture tank; and a sparger that is provided in the second culture tank and releases fine bubbles controlled by the control device.

According to the present invention, the control device controls the sparger actually provided in the second culture tank according to the result of simulation executed based on the culture data acquired in the small-scale first culture tank, and it is not necessary to actually perform the culture experiment of the culturing target material in the second culture tank, and the cost required for the experiment can be greatly reduced.

The control method of the present invention may include PFC control.

According to the present invention, the DO value can be stably controlled near the setting value while suppressing the haunting phenomenon occurring in the PID control by using the PFC control suitable for the process control in which the first-order lag and the dead time exist in the control method for controlling the second culture tank.

The present invention provides a method for designing a culture system including: acquiring culture data over time indicating a relationship between a DO value detected in a culture solution and an oxygen supply amount controlled by a freely-selected control method, the culture solution being stored in a first culture tank in which a culturing target material is cultured; identifying a culture model indicating a relationship between the oxygen supply amount for the culturing target material increasing over time and the DO value, based on the culture data; and executing simulation of virtually culturing the culturing target material in a second culture tank based on the culture model and a control method of culturing the culturing target material based on the oxygen supply amount in the second culture tank, using a calculation device in which a program for executing the control method is installed, and calculating parameters of the control method based on the simulation result.

According to the present invention, by identifying a culture model based on culture data obtained in a first culture tank and executing simulation for controlling a second culture tank based on the culture model, it is possible to adjust parameters of a control method in the second culture tank without actually performing a culture experiment of a culturing target material in the second culture tank, and it is possible to greatly reduce the cost required for the experiment.

The present invention may further include repeatedly executing the simulation using the calculation device and adjusting the parameters based on a relationship between the oxygen supply amount virtually controlled based on the control method and a DO value detected in the second culture tank.

According to the present invention, it is possible to adjust parameters used in a control method in simulation without limiting the number of times without actually performing a culture experiment of a culturing target material in the second culture tank, and it is possible to significantly reduce the cost required for the experiment.

The present invention may further include inputting the parameters to a control device in which a program for executing the control method is installed; and controlling the oxygen supply amount based on the control method to which the parameters are applied using the control device in the actual second culture tank, and adjusting the DO value in the second culture tank to a preset setting value.

According to the present invention, in the control device that actually controls the second culture tank, since the parameters of the control method are adjusted in advance by the calculation device, the second culture tank can be accurately controlled together with the start of operation of the second culture tank without performing an actual culture experiment in the second culture tank.

Advantageous Effects of Invention

According to the present invention, it is possible to calculate a control value of the amount of dissolved oxygen in a culture tank without performing an actual culture experiment of a culturing target material in the culture tank.

DESCRIPTION OF EMBODIMENTS

When a culturing target material such as an animal cell or a microorganism is cultured in a culture tank, various problems occur. For example, the DO control in a culture tank is a process control with a dead time until the control target amount actually appears with respect to the target value, and it is difficult to apply PID control (Proportional-Integral-Differential Controller) generally used in control of a plant or the like. This is because PID control is a type of feedback control, and when it is applied to DO control in a culture tank, it is not suitable to cope with the oxygen consumption amount that increases with the lapse of time with one parameter.

As another culture control method, ON/OFF control is known. In the ON/OFF control, for example, the DO measurement value is compared with the DO setting value in the culture tank, and when the DO measurement value does not reach the DO setting value even after a certain period of time elapses, an arbitrary amount of oxygen supply is controlled to be increased or decreased. However, in the DO control based on the ON/OFF control, the control accuracy becomes very poor, and foaming may easily occur due to excessive supply of oxygen. When foaming occurs at the culture interface due to aeration in the culture tank, it may cause deterioration of growth of microorganisms and animal cells.

Foaming has an adverse effect such as inhibiting the discharge of carbon dioxide gas in the culture solution, blocking the exhaust filter when the foam leaks from the exhaust of the culture tank, floating the microcarrier in culture using the microcarrier which is a microparticle in the culture tank, separating the foam from the microorganism and the animal cell, and reducing the oxygen supply to the microorganism and the animal cell. When a defoaming agent is added in order to eliminate foaming in the culture tank, there is a possibility that the defoaming agent inhibits the growth of a culturing target material and generates a load on the purification step. Therefore, it is desirable to suppress foaming based on ventilation control without using a defoaming agent as much as possible in the culture tank.

Furthermore, when a culture experiment is performed in an actual culture tank in order to calculate a control value of DO control in the culture tank, the scale of the experiment is large, a large amount of cost is required, and a long period of time is required to acquire data. The inventors have intensively studied to perform appropriate DO control in a culture tank without performing large-scale experiments. Hereinafter, a culture management apparatus according to an embodiment of the present invention will be described.

Figure 1:
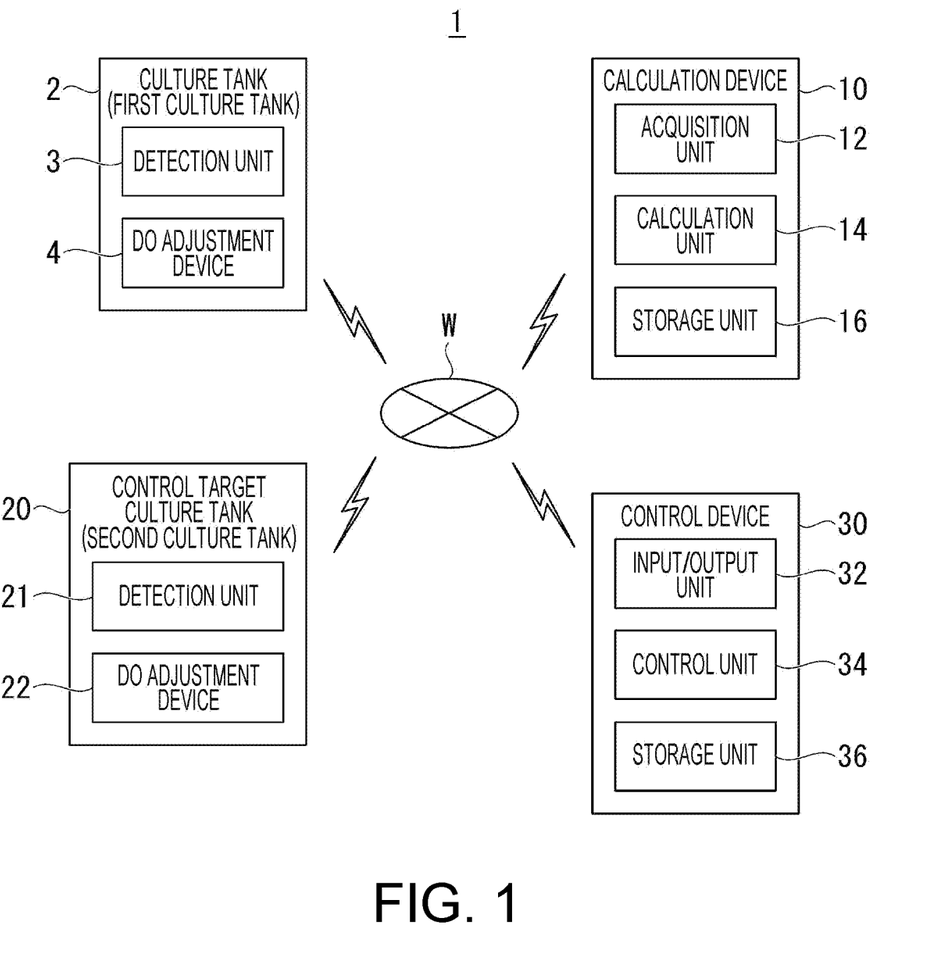
FIG. 1 is a block diagram showing a configuration of a culture system.
Figure 2:
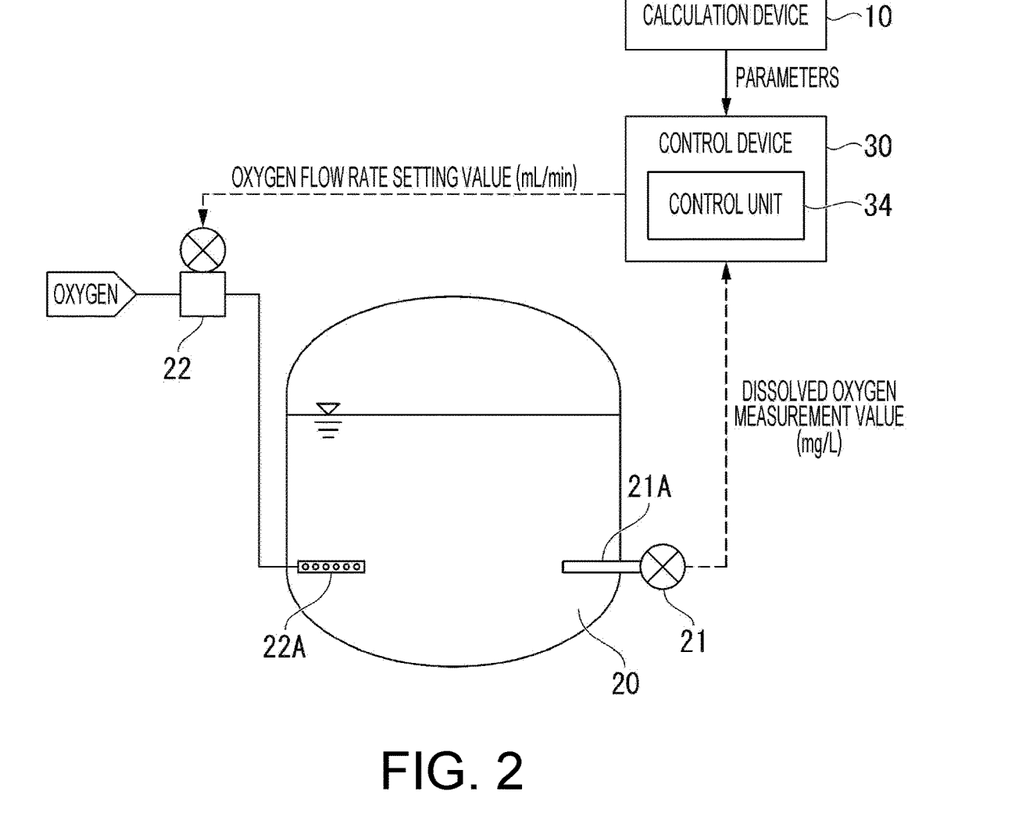
FIG. 2 is a diagram schematically showing a configuration of a control target culture tank.

As shown in FIGS. 1 and 2, a culture system 1 includes a culture tank 2 for experiment (first culture tank), a control target culture tank 20 (second culture tank) for actually culturing a culturing target material, a calculation device 10 that executes simulation for controlling the control target culture tank 20 based on an experimental result of the culture tank 2, and a control device 30 that controls the control target culture tank 20. The culture tank 2 is, for example, a small-scale laboratory culture facility for culturing a culturing target material and measuring culture data based on DO control. The culture tank 2 may be an actual culture facility currently in operation, or may be the control target culture tank 20. That is, any culture tank may be used as the culture tank 2 as long as culture data of the culturing target material can be acquired.

The culture tank 2 includes, for example, a container that stores a culture solution for culturing a culturing target material. The culture tank 2 is provided with a detection unit 3 that detects the amount of dissolved oxygen (DO value) in the culture solution. The detection unit 3 includes, for example, a dissolved oxygen sensor provided in the container. In addition, the culture tank 2 is provided with a DO adjustment device 4 that supplies oxygen into the culture solution. The DO adjustment device 4 includes, for example, a mass flow controller (not illustrated) that supplies oxygen and a sparger (not illustrated). The mass flow controller supplies gaseous oxygen to the sparger via an oxygen supply line. The sparger diffuses gaseous oxygen into the culture solution in the culture tank 2.

The sparger is provided at a distal end of the oxygen supply line connected to the mass flow controller, and is disposed in the culture tank 2. The sparger is formed of, for example, a porous body such as an SPG film, a ceramic film, or a sintered metal. The sparger is configured to supply fine bubbles (microbubbles) of oxygen into the solution through a myriad of pores formed in the porous body, to increase a contact area between the solution and oxygen, and to facilitate dissolution of oxygen in the solution.

The control target culture tank 20 is a large-scale culture facility for actually culturing the culturing target material. The control target culture tank 20 is a newly designed culture tank or an existing culture tank in which the control system is scheduled to be renewed. The control target culture tank 20 is constructed in, for example, a storage container that stores a culture solution for culturing a culturing target material. The control target culture tank 20 is provided with a detection unit 21 that detects the amount of dissolved oxygen in the culture solution. The detection unit 21 includes, for example, a dissolved oxygen sensor provided in the container. In addition, the control target culture tank 20 is provided with a DO adjustment device 22 that supplies oxygen into water. The DO adjustment device 22 includes, for example, a mass flow controller that supplies oxygen and a sparger 22A. The mass flow controller supplies gaseous oxygen to the sparger 22A via an oxygen supply line. The sparger 22A has the above-described configuration and diffuses gaseous oxygen into the culture solution in the control target culture tank 20.

The calculation device 10 is simulation device that executes simulation of virtually culturing a culturing target material in the control target culture tank 20 before operating the large-scale control target culture tank 20. The calculation device 10 is realized by an information processing terminal device including a control device such as a personal computer, a tablet terminal, or a smartphone. The calculation device 10 is communicably connected to the culture tank 2. The calculation device 10 may be connected to the culture tank 2 via a network W. The network W includes, for example, a public network and a local area network (LAN). The calculation device 10 may be a server device connected to the network W. The calculation device may be a system on a cloud connected to the network W. The calculation device 10 acquires culture data from the culture tank 2. The calculation device 10 may not be connected to the culture tank 2, and may acquire culture data from the culture tank 2 based on a recording medium on which data is recorded.

The culture data is data over time indicating the relationship between the DO value detected at time t and the oxygen supply amount in the culture solution stored in any culture tank 2 in which the culturing target material is cultured. The culture data does not need to include cell growth data, and may indicate the relationship between the DO value and the oxygen supply amount controlled by any control method such as conventional ON/OFF control in culturing the culturing target material. That is, the culture data is obtained in the process of culturing the culturing target material, and can be used regardless of the control method as long as it is data in which the oxygen supply amount and the DO value at time t are continuously indicated and a state in which the oxygen supply amount increases with the lapse of time is indicated. Therefore, the culture data is not limited to the experimental data, and may be data acquired from a currently operating culture tank or data acquired from a culture tank in the past.

The calculation device 10 acquires culture data of the culturing target material cultured in the culture tank 2 from an acquisition unit 12. The acquisition unit 12 includes a communication interface for transmitting and receiving communication data, a drive device capable of reading a storage medium in which data is recorded, and the like. The data acquired from the acquisition unit 12 is stored in a storage unit 16. The storage unit 16 stores data and programs used for calculation and control. The storage unit 16 includes a storage medium such as a hard disk drive (HDD), a flash memory, or a solid state drive (SSD). The storage unit 16 may be a virtual server device on a cloud connected to the network W.

The data stored in the storage unit 16 is read by a calculation unit 14, and calculation is executed. For example, the calculation unit 14 identifies a culture model indicating a relationship over time between the oxygen supply amount to be supplied to the culturing target material, which increases over time, and a virtual DO value based on the acquired culture data. The culture model is, for example, a temporal model approximated by a simple formula that calculates a virtual DO value detected in a first-order lag response after a predetermined time when an oxygen supply amount is input. As the culture model, any culture model may be used as long as the relationship between the oxygen supply amount and the virtual DO value can be reproduced over time.

The culture model is identified by adjusting parameters included in a predetermined formula so that a virtual DO value calculated by inputting actual oxygen supply amount data approaches an actual measurement value of the DO value. The adjustment of the culture model may be performed manually based on the culture data, or may be automatically performed by the calculation unit 14 based on machine learning using a large number of pieces of culture data as teacher data.

The calculation unit 14 executes simulation of virtually culturing the culturing target material in the control target culture tank 20 using the identified culture model and a predetermined culture control method set in advance. In the culture control method, an oxygen supply amount is adjusted so as to culture a culturing target material, and a DO value is controlled based on a predetermined algorithm so as to approach a setting value. As the culture control method, for example, PFC control (Predictive Functional Control) suitable for process control in which there is first-order lag+dead time in the culture tank is used.

PFC control is one of various types of model predictive control (MPC). The PFC control is a control method in which the movement of the control target (DO value) is predicted on the assumption that the output of the control target DO value makes a temporary delay response to the input (oxygen supply amount: MV value), and the system (culture amount) is optimized to stably operate.

In the PFC control, a setting value to be a control target is set. In the present embodiment, the setting value is a target DO value. Next, a curve called a reference trajectory that ideally approximates the current DO value with respect to the setting value is defined. The reference trajectory is set by, for example, an exponential function. A point called a coincidence point is set on the trajectory of the reference trajectory. The PFC control performs the optimum control based on the oxygen supply amount so as to minimize the difference between the prediction value of the control target value and the value of the reference trajectory at the coincidence point.

As the culture control method, other algorithms such as ON/OFF control and PID control may be used as long as the oxygen supply amount is controlled. The calculation unit 14 executes simulation using a culture control method based on a control program for controlling the DO adjustment device 22 to adjust the oxygen supply amount. The calculation unit 14 executes simulation based on a setting value such as the input design value of the control target culture tank the amount of the culture solution accommodated in the control target culture tank 20, and the control amount of the DO adjustment device 22. The calculation unit 14 executes control to control the oxygen supply amount (MV value) based on the culture control method in the simulation and maintain the DO value at a target value (setting value).

In the simulation, the calculation unit 14 calculates the DO value virtually detected with respect to the virtual oxygen supply amount (MV value) supplied to the control target culture tank based on the culture model. For the DO value virtually detected, the calculation unit 14 calculates a virtual oxygen supply amount so as to control the virtual DO value to a target value based on the culture control method. The calculation unit 14 executes simulation for supplying the calculated virtual oxygen supply amount to the control target culture tank 20, and calculates a DO value virtually detected. The calculation unit 14 executes simulation. The calculation unit 14 repeatedly executes simulation for repeating the above processing, and adjusts the parameters based on the relationship between the oxygen supply amount virtually controlled based on the culture control method and the DO value detected in the control target culture tank 20.

According to the calculation device 10, the culture prediction of the culturing target material can be performed without performing a large-scale culture experiment by performing simulation in advance before actually operating the control target culture tank 20. According to the calculation device 10, it is possible to execute simulation and adjust the parameters used in the culture control method without performing a large-scale culture experiment. The data of the adjusted parameters is input to the control device 30, for example, in order to control the actual control target culture tank 20 via the network W.

The control device 30 is connected to the control target culture tank 20 via, for example, the network W. The control device 30 is realized by, for example, an information processing terminal device including a control device such as a personal computer, a tablet terminal, a smartphone, or a programmable logic controller (PLC), a sequencer that controls a control target device, or the like. The control device 30 acquires the parameters from an input/output unit 32. The input/output unit 32 includes a communication interface that transmits and receives communication data, a device that inputs and outputs a data signal, a drive device that can read a storage medium in which data is recorded, and the like.

The input/output unit 32 also acquires data of the amount of dissolved oxygen (DO value) in the culture solution detected from the detection unit 21 of the control target culture tank 20, and stores the data in a storage unit 36. The data acquired from the input/output unit 32 is stored in the storage unit 36. The storage unit 36 further stores data and programs used for calculation and control. The storage unit 36 includes a storage medium such as a hard disk drive (HDD), a flash memory, or a solid state drive (SSD).

The data stored in the storage unit 36 is read by a control unit 34 and controls the actual control target culture tank 20. A program for executing the culture control method is installed in the storage unit 36. The control unit 34 reads the program from the storage unit 36 and executes the culture control method. In the actual control target culture tank 20, the control unit 34 controls the oxygen supply amount based on the culture control method to which the input parameters are applied. The control unit 34 controls the oxygen supply amount based on the culture control method based on the detection value of the DO value of the detection unit 21, and adjusts the DO value in the control target culture tank 20 to a preset setting value.

The control unit 34 generates a control signal for controlling the DO adjustment device 22. The control signal is a signal for controlling the DO adjustment device 22. The control unit 34 outputs a control signal from the input/output unit 32, controls the DO adjustment device 22, and adjusts the oxygen supply amount to be supplied to the control target culture tank 20. Specifically, the control unit 34 controls the sparger 22A that releases the fine bubbles to the control target culture tank 20 to adjust the oxygen supply amount in the culture solution. The control unit 34 controls the DO adjustment device 22 based on the program stored in the storage unit 36. The control unit 34 cultures the culturing target material based on the PFC control in the control target culture tank 20.

The control target culture tank 20 is provided with the detection unit 21. The detection unit 21 measures the amount of dissolved oxygen (mg/L) in the control target culture tank 20 using a DO meter 21A, and outputs a detection value to the calculation device 10. In the calculation device 10, the calculation unit 14 compares the set DO setting value with the DO measurement value detected by the detection unit 3, and calculates the oxygen supply amount (mL/min) using the PFC control.

The control unit 34 generates a control signal based on the calculation value of the oxygen supply amount, and outputs the control signal to the mass flow controller of the oxygen supply line provided in the DO adjustment device 22. The mass flow controller supplies gaseous oxygen to the sparger 22A via an oxygen supply line. The gaseous oxygen is diffused from the sparger 22A into the culture solution in the control target culture tank 20.

In the present embodiment, in the PFC control, the calculation formula of the model predictive control is directly written into the program of the sequencer connected to the control unit 34 and processing is performed without using the model predictive control software. The sequencer can perform arithmetic processing at a cycle of several milliseconds. The sequencer in the present embodiment is configured to perform arithmetic processing in a cycle of one second, for example. Therefore, when the oxygen flow rate (oxygen consumption by the cells) increases according to the growth of the cells with the lapse of time in the control target culture tank 20, the sequencer calculates an appropriate oxygen flow rate at a cycle of 1 second. As a result, the control unit 34 can output the operation amount substantially in real time to the mass flow controller that controls the oxygen flow rate. In an initial predetermined period when the culturing target material is cultured using the actual control target culture tank 20, the parameters used in the culture control method are appropriately adjusted based on the detection value of the DO value.

According to the culture system 1, even in the culture step performed for about 7 to 10 days, control can be performed with control accuracy of about ±0.1 to 0.2 mg/L (actual value) with respect to the DO setting value continuously during the culture period.

Next, each step of the culture management method in the culture system 1 will be described.

Figure 3:
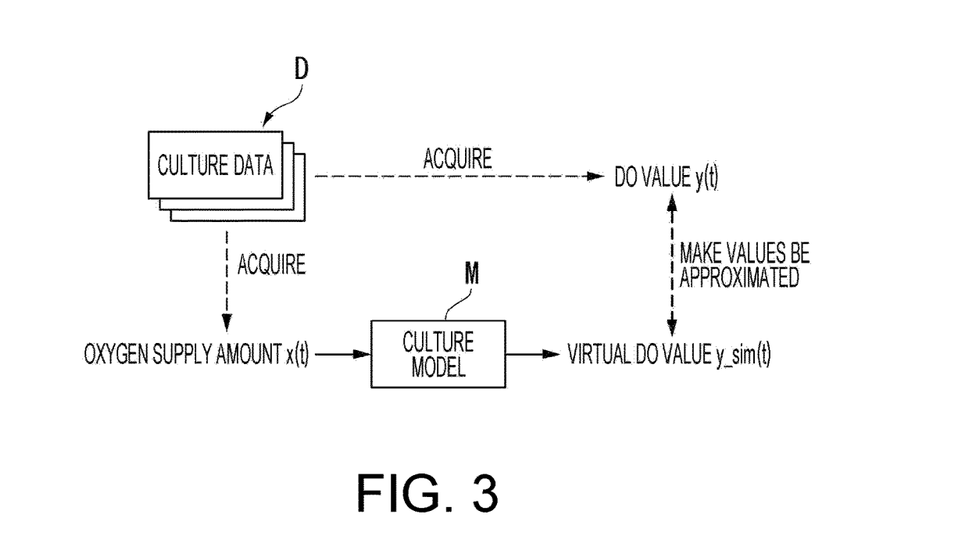
FIG. 3 is a view conceptually illustrating a method for identifying a culture model.

As shown in FIG. 3, when the PFC control is applied to the DO control of the control target culture tank 20, culture data D indicating the relationship between the oxygen supply amount and the DO value at time t is acquired based on a culture test using the small-scale laboratory culture tank 2 in advance before operating the control target culture tank 20. The calculation unit 14 identifies the culture model M for calculating the virtual DO value when the oxygen supply amount x(t) at time t is supplied. The initial parameters of the culture model M are set so as to calculate the virtual DO value based on the oxygen supply amount at time t.

For example, the calculation unit 14 acquires the oxygen supply amount x(t) at time t based on the culture data D. The calculation unit 14 inputs the acquired oxygen supply amount x(t) to the culture model M in which the initial parameters are set, and calculates a virtual DO value y_sim(t). The calculation unit 14 adjusts the initial parameters of the culture model M so that the measured DO value y(t) detected for the oxygen supply amount x(t) at time t obtained based on the culture data D approximates the calculated virtual DO value y_sim(t), and identifies the culture model M. The initial parameters are adjusted, for example, to minimize an error between the DO value y(t) and the virtual DO value y_sim(t).

Next, the calculation unit 14 executes simulation of virtually culturing the culturing target material based on the PFC control while reproducing the growth of the culturing target material using the culture model in the virtual control target culture tank 20. The PFC control includes a plurality of parameters that can be arbitrarily set. Before actually culturing the culturing target material in the control target culture tank 20, it is necessary to adjust the parameters used in the PFC control according to the target process.

In normal plant facility, parameters are tuned at the time of trial operation using water or the like, and then the parameters are finely adjusted in the course of operation using the real solution to optimize the parameters. However, the dissolved oxygen control used in the culture step of culturing the culturing target material cannot reproduce the control behavior unless an experiment is performed using oxygen-consuming cells. In addition, the culture medium and the cells are very expensive, and it is difficult to tune the parameters of the culture control method while actually culturing the culturing target material.

Therefore, in the culture system 1, the calculation device 10 executes simulation for culturing the culturing target material based on the PFC control in advance, and adjusts the parameters used for the PFC control in a state where the control device 30 and the control target culture tank 20 are offline. The parameters used for the PFC control may be optimized by constructing a culture model again based on the experimental result of actually culturing the culturing target material and performing simulation based on the PFC control.

Figure 4:
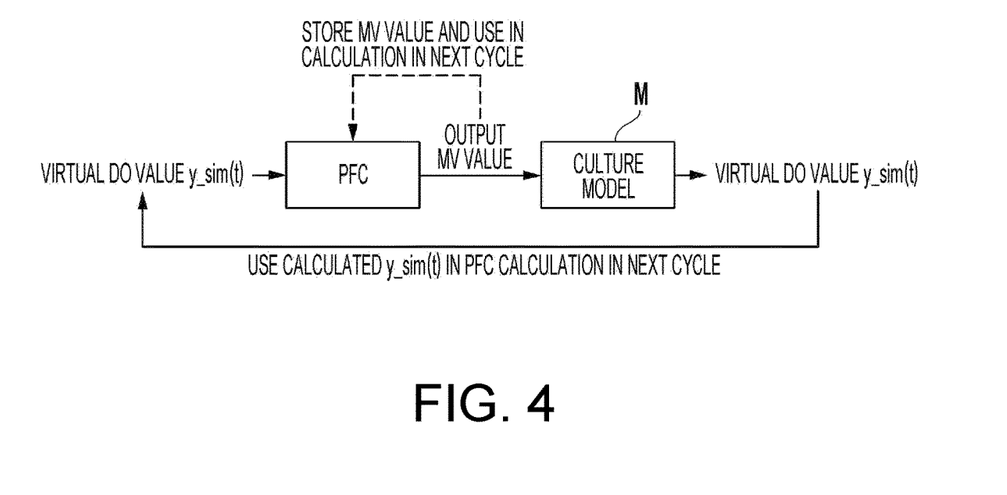
FIG. 4 is a diagram conceptually illustrating simulation executed in a calculation device.

FIG. 4 illustrates a flow of simulation based on the PFC control executed by the calculation unit 14. The calculation unit 14 calculates the oxygen supply amount (MV value) with respect to the DO value detected at time t based on the PFC control in the virtual control target culture tank 20. The calculation unit 14 stores the calculated MV value in the storage unit 16 for use in calculation in the next cycle. The calculation unit 14 applies the calculated MV value to the culture model M, virtually grows the culturing target material, and calculates a virtual DO value predicted to be detected by the detection unit 21.

The calculation unit 14 reads the previously-calculated MV value from the storage unit 16, calculates a new MV value based on the calculated virtual DO value and the previously-calculated MV value, and applies the new MV value to the culture model to calculate a new virtual DO value. The calculation unit 14 repeatedly executes the above calculation in the simulation and outputs a result. It can be confirmed that the results of the simulation based on the PFC control can be stably controlled by visualizing the results with a graph.

Figure 5:
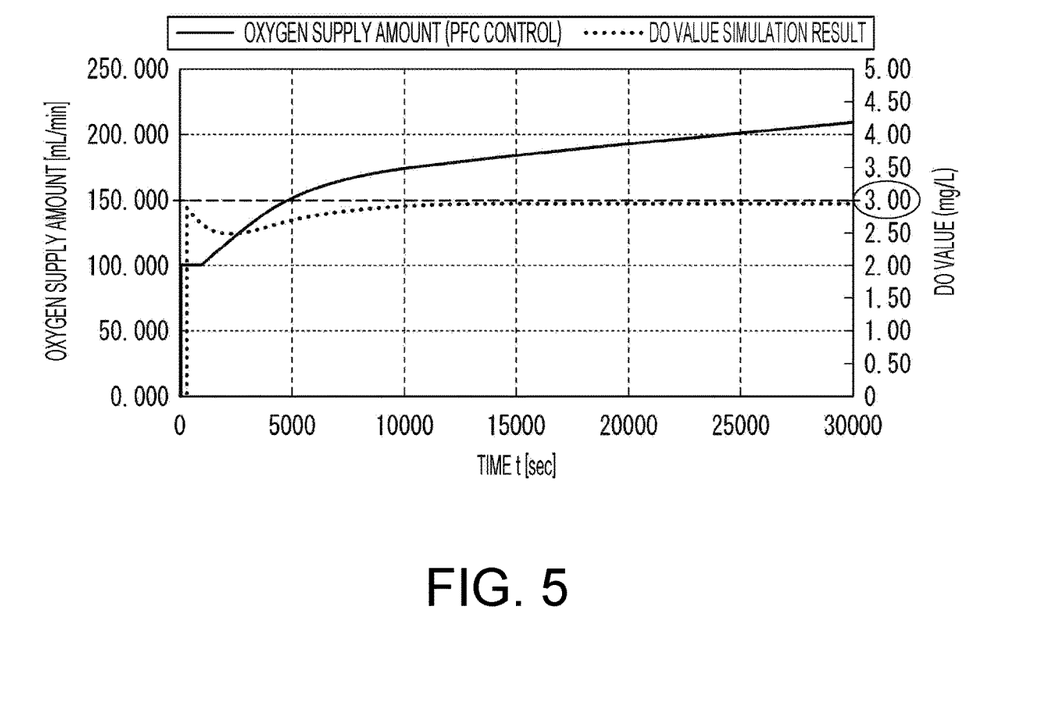
FIG. 5 is a diagram illustrating an example of simulation result.

FIG. 5 illustrates an example of a result of simulation based on the PFC control. The simulation is performed for 8.3 hours (30,000 seconds), for example. As illustrated in the drawing, a state in which the culturing target material (cell) grows over time and the oxygen consumption increases accordingly is reproduced by simulation based on the culture model. In the case of the normal PID control, an overshoot at the rise of the oxygen flow rate and a subsequent haunting phenomenon occur. On the other hand, when applied to the control of the DO value, the PFC control can stably control the DO value near the setting value while suppressing the haunting phenomenon occurring in the PID control.

The DO value is stably controlled to a value of 2.94 mg/L with respect to a target value of 3.00 mg/L after a lapse of a predetermined time from an initial state. This indicates that the control accuracy is controlled at the full scale accuracy of 0.6% with respect to the setting range of 0 to 10 mg/L. As illustrated in the drawing, the PFC control can stably control the DO value to a value close to the target value even in a case where the oxygen consumption amount increases as the control target material grows with the lapse of time. According to the PFC control, the oxygen supply amount can be optimized, and foaming based on excessive oxygen supply into the culture solution can be prevented.

Figure 6:
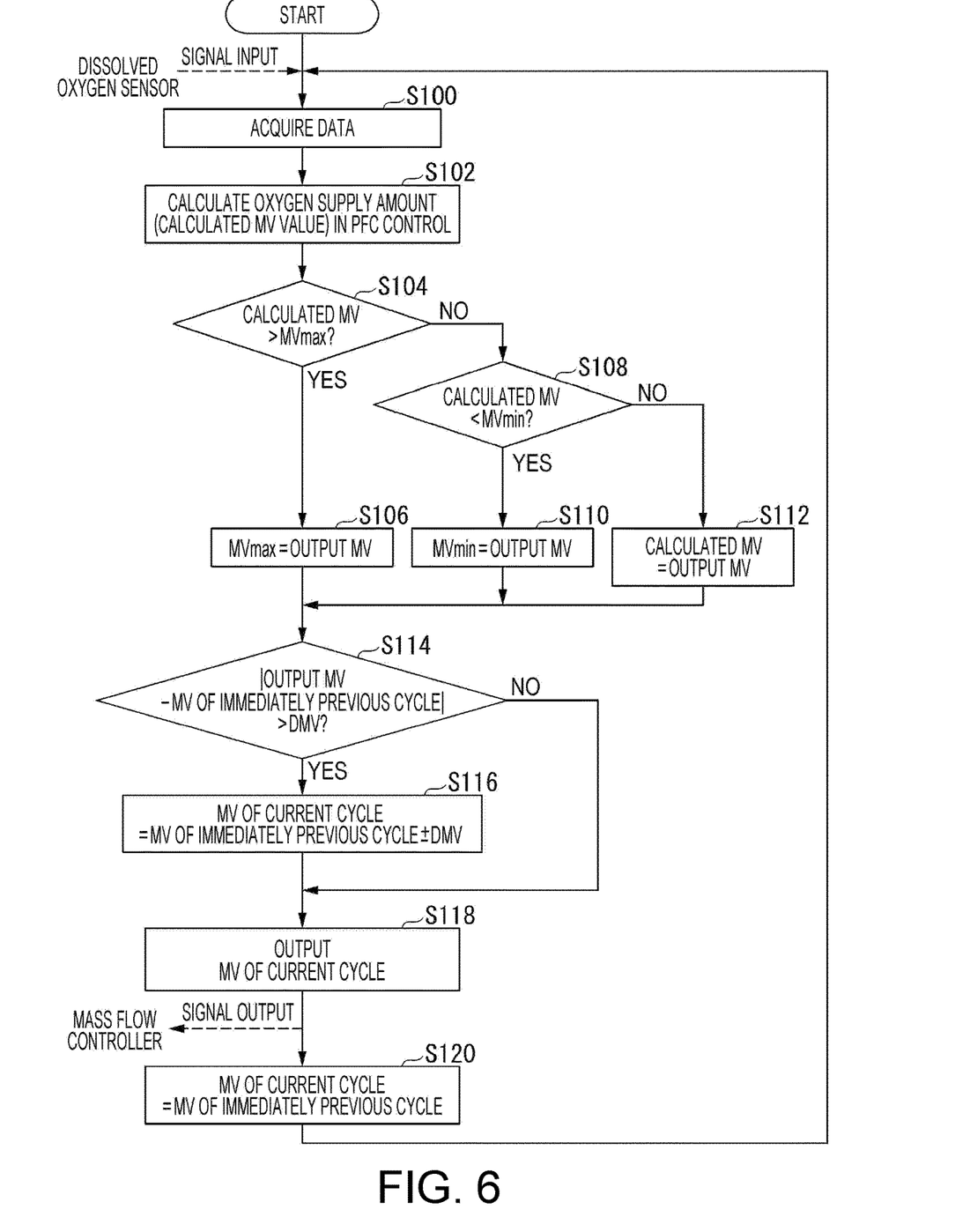
FIG. 6 is a flowchart illustrating each process of simulation of PFC control executed in the calculation device.

FIG. 6 illustrates each process of the simulation based on the PFC control executed in the calculation device 10. The PFC control described below is executed in the simulation, and is also executed in the actual control of the control target culture tank 20. The PFC control of the embodiment predicts the movement of the control target (DO value) assuming that the control target (DO value) makes a temporary delay response, repeatedly calculates the oxygen supply amount (MV value) so as to perform a stable operation, and optimizes the parameters. In the DO control of the control target culture tank 20, for example, a calculation formula of the PFC control for "integral+first-order lag dead time process" is adopted. The PFC control of the embodiment repeatedly calculates the oxygen supply amount (MV value) over time as described below.

In the calculation of the oxygen supply amount (MV value) based on the PFC control, the calculation unit 14 acquires data set with arbitrary parameters as an initial value of the MV value at the time of the first cycle calculation, and acquires data of the MV value of an immediately previous cycle when there is the MV value of the immediately previous cycle (step S100). The calculation unit 14 inputs the initial value of the MV value to the culture model to calculate a virtual DO value in the control target culture tank 20 (see FIG. 4), and calculates an oxygen supply amount (MV value) with respect to the virtual DO value based on the PFC control as the calculated MV value (step S102). The calculated MV value is not stable immediately after the activation of the PFC control or when disturbance occurs, and may excessively increase or decrease as compared with the MV value of the immediately previous cycle.

Therefore, the calculation unit 14 does not output the calculated MV value as it is, but compares the MV upper limit (=MVmax), which is an arbitrarily settable parameter, with the calculated MV value to determine whether the calculated MV value is larger than the MV upper limit (step S104). When the calculated MV value is larger than the MV upper limit, the calculation unit 14 outputs the MV upper limit as the output MV value (step S106). If the calculated MV value is less than or equal to the MV upper limit (step S104: No), the calculation unit 14 compares the calculated MV value with the MV lower limit (=MVmin), which is an arbitrarily settable parameter, and determines whether the calculated MV value is less than the MV lower limit (step S108).

When the calculated MV value is less than the MV lower limit (step S108: Yes), the calculation unit 14 outputs the MV lower limit as the output MV value (step S110). When the calculated MV value is greater than or equal to the MV lower limit value (step S108: No), the calculation unit 14 outputs the calculated MV value as the output MV value (step S112). The calculation unit 14 compares the difference between the output MV value and the MV value of the immediately previous cycle with the arbitrarily settable parameter DMV, and determines whether the difference is larger than the DMV (step S114).

When the difference between the output MV value and the MV value of the immediately previous cycle is larger than the DMV (step S114: Yes), the calculation unit 14 outputs a value obtained by adding (or subtracting) the DMV to (from) the output MV value as the MV value of a current cycle (step S116). When the difference between the output MV value and the MV value of the immediately previous cycle is equal to or less than the DMV (step S114: No), the calculation unit 14 outputs the output MV value as the MV value of the current cycle (step S118). The calculation unit 14 stores the output MV value of the current cycle in the memory in the sequencer as the MV value of the immediately previous cycle and uses the MV value in the PFC control calculation formula of the next cycle (step S120). The calculation unit 14 returns the processing to step S100, repeatedly executes the above simulation steps, and accumulates simulation data over time (see FIG. 5).

The accumulated simulation result is output to a graph in the calculation device 10, visualized, and verified. In the calculation device 10, the simulation result is verified, and the parameters based on the PFC control are appropriately adjusted based on the relationship between the MV value controlled based on the PFC control and the virtual DO value detected in the control target culture tank 20 so that the virtual DO value is stably controlled. The parameters adjusted by the calculation device 10 are input to the control device 30 after the actual control target culture tank 20 is constructed, and the culturing target material is actually cultured and verified in the control target culture tank 20.

A program for executing the PFC control is installed in the control device 30. The adjusted parameters are input to the control device 30. After the parameters are input, the control device 30 controls the sparger 22A that releases fine bubbles into the control target culture tank 20 based on the PFC control to which the parameters are applied in the actual control target culture tank 20 to control the oxygen supply amount (MV value). Based on the DO value detected by the detection unit 21, the control device 30 controls the sparger 22A to adjust the oxygen supply amount (MV value), and adjusts the DO value in the control target culture tank 20 to a preset setting value. The detection result is stored in the storage unit 36 during the verification period.

The accumulated experimental results are input to the calculation device 10. The calculation device 10 outputs the experimental results to a graph and visualizes the experimental results. In the calculation device 10, the experimental result is verified, and the parameters based on the PFC control are finely adjusted again based on the relationship between the MV value controlled based on the PFC control and the actual DO value detected in the control target culture tank 20 so that the actual DO value is stably controlled.

According to the culture system 1, by applying the PFC control to the culture of the culturing target material, oxygen can be stably and continuously supplied in the control target culture tank 20 as compared with a conventional control method such as ON/OFF control. According to the culture system 1, the oxygen supply amount is gradually increased with respect to the increase in the oxygen consumption amount accompanying the increase in the number of cells and microorganisms, whereby the DO value can be controlled with high accuracy near the setting value without haunting.

According to the culture system 1, the oxygen supply amount can be supplied to the cells in the minimum necessary amount, and foaming in the culture tank due to oxygen supply can be suppressed. Specifically, in order to efficiently dissolve oxygen into the culture solution, oxygen is preferably supplied in the state of fine bubbles such as microbubbles. For example, in the present embodiment, oxygen is supplied from the sparger in the state of fine bubbles having a bubble diameter of 0.5 to several 100 μm. However, when oxygen is formed into fine bubbles, bubbles are easily generated. Therefore, it is more important that oxygen of the fine bubbles is supplied in a minimum necessary amount. According to the culture system 1, by using the PFC control, the oxygen supply amount can be adjusted with high accuracy (the necessary amount is supplied), and thus, even if oxygen is supplied in the state of fine bubbles, foaming can be suppressed. Along with this, the oxygen consumption amount can also be suppressed. According to the culture system 1, by suppressing foaming, it is possible to avoid microcarriers from being caught in bubbles even in cell culture using microcarriers.

According to the culture system 1, a culture model can be identified based on culture data obtained from the small-scale laboratory culture tank 2. According to the culture system 1, the control parameters can be examined offline by executing simulation of culturing a culturing target material based on the PFC control in the calculation device 10. According to the culture system 1, it is possible to perform control with high accuracy in actual culture based on parameters obtained in simulation. According to the culture system 1, it is not necessary to perform an experiment in the large-scale control target culture tank 20, and it is possible to greatly reduce the cost until the culturing target material is actually cultured.

According to the culture system 1, it is possible to identify a culture model based on culture data and execute simulation regardless of the scale of a culture tank and a control method. According to the culture system 1, it is possible to design another culture tank (third culture tank) that expands the scale of the control target culture tank 20 currently in operation. That is, according to the culture system 1, simulation in the third culture tank that expands the second culture tank can be executed based on culture data obtained by culturing a culturing target material in the second culture tank, and the performance of the third culture tank can be evaluated based on the simulation result. In this case, the third culture tank is not limited to the same scale as the second culture tank, and may be set at any scale.

Some or all of the components of the calculation device 10 described above are realized, for example, by a hardware processor such as a central processing unit (CPU) executing a program (software). Some or all of these components may be installed in hardware (circuit unit; including circuitry) such as a large scale integration (LSI), an application specific integrated circuit (ASIC), a field-programmable gate array (FPGA), or a graphics processing unit (GPU), or by cooperation of software and hardware.

The program may be stored in advance in a storage device such as a hard disk drive (HDD), an SSD, or a flash memory, or may be stored in a removable non-transitory storage medium such as a DVD, a CD-ROM, or a flash memory, and may be installed by attaching the storage medium to the drive device. Furthermore, the computer program may be distributed to a computer via a communication line, and the computer that has received the distribution may execute the program.

Although the embodiments for carrying out the present invention have been described above using the embodiments, the present invention is not limited to these embodiments at all, and various modifications and substitutions can be made without departing from the gist of the present invention. For example, the calculation unit 14 may control the control target culture tank 20 while executing simulation based on not only the PFC control but also another culture control method. The calculation unit 14 may perform machine learning based on culture data, execute simulation based on the learning result, and control the control target culture tank 20.

The control device 30 may control a plurality of control target culture tanks 20. The calculation device 10 may acquire culture data from a plurality of culture tanks 2 or a plurality of control target culture tanks 20 in an integrated manner. The calculation device 10 may execute a plurality of simulations for the plurality of control target culture tanks 20 in an integrated manner. The calculation device 10 may appropriately execute simulation based on culture data recorded at a predetermined timing such as after the lapse of a predetermined period in which the control target culture tank 20 is operated, and adjust parameters used for the PFC control. The control device may be replaced with a control device of the existing control target culture tank 20.

The invention claimed is:

1. A calculation device comprising
a calculation unit configured to: acquire culture data over time indicating a relationship between a DO value detected in a culture solution and an oxygen supply amount controlled by a freely-selected control method, the culture solution being stored in a first culture tank in which a culturing target material is cultured; identify a culture model indicating a relationship between the oxygen supply amount increased or decreased along with the culturing target material increasing over time and the DO value, based on the culture data; and execute simulation of virtually controlling the oxygen supply amount so as to keep the DO value in a second culture tank at a preset setting value and culturing the culturing target material in the second culture tank using a culture control method of culturing the culturing target material based on the culture model and the oxygen supply amount in the second culture tank, and calculate parameters to be used for controlling the oxygen supply amount and/or the DO value in the culture control method based on the simulation result.

2. The calculation device according to claim 1, wherein the calculation unit identifies the culture model calculating the DO value detected in a first-order lag response after a predetermined time when the oxygen supply amount is input, repeatedly executes the simulation for controlling the oxygen supply amount so as to keep the DO value in the second culture tank at the preset setting value while controlling to increase or decrease the oxygen supply amount required in the second culture tank in accordance with an oxygen consumption amount increasing or decreasing with a virtual increase or decrease of the culturing target material, and adjusts the parameters based on a relationship between the oxygen supply amount virtually controlled based on the culture control method and the DO value detected in the second culture tank.

3. A control device in which a program for executing the culture control method in the calculation device according to claim 1 is installed, the control device comprising:
a control unit that controls the oxygen supply amount based on the culture control method to which the parameters are applied in the actual second culture tank after the parameters are input, and adjusts the DO value in the second culture tank to a preset setting value.

4. The control device according to claim 3, wherein the control unit controls a sparger that releases fine bubbles into the second culture tank to adjust the oxygen supply amount.

5. A culture system comprising:
a calculation device comprising a calculation unit configured to: acquire culture data over time indicating a relationship between a DO value detected in a culture solution and an oxygen supply amount controlled by a freely-selected control method, the culture solution being stored in a first culture tank in which a culturing target material is cultured; identify a culture model indicating a relationship between the oxygen supply amount increased or decreased along with the culturing target material increasing over time and the DO value, based on the culture data; and execute simulation of virtually controlling the oxygen supply amount so as to keep the DO value in a second culture tank at a preset setting value and culturing the culturing target material in the second culture tank using a culture control method of culturing the culturing target material based on the culture model and the oxygen supply amount in the second culture tank, and calculate parameters to be used for controlling the oxygen supply amount and/or the DO value in the culture control method based on the simulation result;

the control device according to claim 3;

the second culture tank; and a sparger that is provided in the second culture tank and releases fine bubbles controlled by the control device.

6. The culture system according to claim 5, wherein the culture control method includes PFC control.

7. A method for designing a culture system comprising:

acquiring culture data over time indicating a relationship between a DO value detected in a culture solution and an oxygen supply amount controlled by a freely-selected control method, the culture solution being stored in a first culture tank in which a culturing target material is cultured;

identifying a culture model indicating a relationship between the oxygen supply amount increased or decreased along with the culturing target material increasing over time and the DO value, based on the culture data; and executing simulation of virtually controlling the oxygen supply amount so as to keep the DO value in a second culture tank at a preset setting value and culturing the culturing target material in the second culture tank based on the culture model and a culture control method of culturing the culturing target material based on the oxygen supply amount in the second culture tank, using a calculation device in which a program for executing the culture control method is installed, and calculating parameters to be used for controlling the oxygen supply amount and/or the DO value in the culture control method based on the simulation result.

8. The method for designing the culture system according to claim 7, further comprising:

identifying the culture model calculating the DO value detected in a first-order lag response after a predetermined time when the oxygen supply amount is input, repeatedly executing the simulation for controlling the oxygen supply amount so as to keep the DO value in the second culture tank at the preset setting value while controlling to increase or decrease the oxygen supply amount required in the second culture tank in accordance with an oxygen consumption amount increasing or decreasing with a virtual increase or decrease of the culturing target material using the calculation device, and adjusting the parameters based on a relationship between the oxygen supply amount virtually controlled based on the culture control method and a DO value detected in the second culture tank.

9. The method for designing the culture system according to claim 8, further comprising:

inputting the parameters to a control device in which a program for executing the culture control method is installed; and controlling the oxygen supply amount based on the culture control method to which the parameters are applied using the control device in the actual second culture tank, and adjusting the DO value in the second culture tank to a preset setting value.

10. A control device in which a program for executing the culture control method in the calculation device according to claim 2 is installed, the control device comprising:

a control unit that controls the oxygen supply amount based on the culture control method to which the parameters are applied in the actual second culture tank after the parameters are input, and adjusts the DO value in the second culture tank to a preset setting value.

11. The control device according to claim 10, wherein the control unit controls a sparger that releases fine bubbles into the second culture tank to adjust the oxygen supply amount.

12. A culture system comprising:

a calculation device comprising a calculation unit configured to: acquire culture data over time indicating a relationship between a DO value detected in a culture solution and an oxygen supply amount controlled by a freely-selected control method, the culture solution being stored in a first culture tank in which a culturing target material is cultured; identify a culture model indicating a relationship between the oxygen supply amount increased or decreased along with the culturing target material increasing over time and the DO value, based on the culture data; and execute simulation of virtually controlling the oxygen supply amount so as to keep the DO value in a second culture tank at a preset setting value and culturing the culturing target material in the second culture tank using a culture control method of culturing the culturing target material based on the culture model and the oxygen supply amount in the second culture tank, and calculate parameters to be used for controlling the oxygen supply amount and/or the DO value in the culture control method based on the simulation result;

the control device according to claim 10;

the second culture tank; and a sparger that is provided in the second culture tank and releases fine bubbles controlled by the control device.

13. The culture system according to claim 12, wherein the culture control method includes PFC control.

* * * * *